(12) United States Patent
Moon et al.

(10) Patent No.: US 11,174,240 B2
(45) Date of Patent: Nov. 16, 2021

(54) CRYSTALLINE SOLID COMPOUND OF 3-PHENYL-4-PROPYL-1-(PYRIDIN-2-YL)-1H-PYRAZOL-5-OL HYDROCHLORIDE

(71) Applicant: Aptabio Therapeutics Inc., Gyeonggi-do (KR)

(72) Inventors: Sung Hwan Moon, Gyeonggi-do (KR); Soo Jin Lee, Gyeonggi-do (KR); Sung Chan Lee, Gyeonggi-do (KR)

(73) Assignee: Aptabio Therapeutics Inc., Gyeonggi-do (KR)

( * ) Notice: Subject to any disclaimer, the term of this patent is extended or adjusted under 35 U.S.C. 154(b) by 177 days.

(21) Appl. No.: 16/605,380

(22) PCT Filed: Apr. 20, 2018

(86) PCT No.: PCT/KR2018/004604
§ 371 (c)(1),
(2) Date: Oct. 15, 2019

(87) PCT Pub. No.: WO2018/194416
PCT Pub. Date: Oct. 25, 2018

(65) Prior Publication Data
US 2021/0122726 A1   Apr. 29, 2021

(30) Foreign Application Priority Data

Apr. 20, 2017 (KR) .................. 10-2017-0050924

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/04; C07B 2200/13
See application file for complete search history.

(56) References Cited

U.S. PATENT DOCUMENTS

2014/0088152 A1  3/2014  Bae et al.
2014/0128418 A1  5/2014  Bae et al.

FOREIGN PATENT DOCUMENTS

| JP | 2003-519698 A | 6/2003 |
| JP | 2014-506920 A | 3/2014 |
| KR | 10-2012-0098462 A | 9/2012 |
| KR | 10-2012-0098489 A | 9/2012 |
| KR | 10-1280160 | 6/2013 |
| KR | 10-1280198 B1 | 6/2013 |
| KR | 10-2014-0027833 A | 3/2014 |
| KR | 10-1633957 | 6/2016 |
| KR | 10-2017-0024083 A | 3/2017 |
| WO | 2014/035070 A1 | 3/2014 |

OTHER PUBLICATIONS

Alfadda. Journal of Biomedicine and Biotechnology, 2012, 1-14 (Year: 2012).*
Bartosz. Biochemical Pharmacology, 2009, 77, 1303-1315 (Year: 2009).*
Klibanski. JAMA, 2001, 285 (6), 785-795 (Year: 2001).*
Soldatos. Diabetes Research and Clinical Practice, 2008, 825, s75-s79 (Year: 2008).*
Golgert. Clinical Journal of the American Society of Nephrology, 2008, 3, 800-807 (Year: 2008).*
Joo, J. B. et al., "A Novel Pyrazole Derivative Protects from Ovarlectomy-induced Osteoporosis through the Inhibition of NADPH Oxidase", Scientific Reports, 2016, vol. 6, article No. 22389. inner pp. 1-14.
International Search Report issued in PCT/KR2018/004604 dated Aug. 10, 2018.
Mino R. Caira, «Crystalline Polymorphism of Organic Compounds», Topics in Current Chemistry, vol. 198, pp. 163-208,1998, DOI: 10,1007/3-540-69178-2_5 (pp. 165-166).
Sherry L. Morisette et al.: "High-throughput crystallization: polymorphs, salts, co-crystals and solvates of pharmaceutical solids", Advanced drug delivery reviews, 2004, v.56, pp. 275-300 (section 1; 3.1).
J. Bernstein "Polymorphism of molecular crystals" Moscow, Nauka, 2007, chapter 7.3.2. Bioavailability pp. 324-330.
T.G. Horuzhaya, V.S. Chuchalin "Biopharmacy—a scientific direction in the development and improvement of drugs", Textbook for students of the Faculty of Pharmacy, 2006, pp. 6-7.
"Chemical Encyclopedic Dictionary", Moscow, "Soviet Encyclopedia", 1983, p. 186 (with machine translation).
Office Action issued corresponding Russian Patent Application No. RU 2019132946, dated Feb. 28, 2020.
Examination Report issued in corresponding Australian Patent Application No. AU 2018256259, dated Mar. 10, 2020.
G.A. Melent'eva, L.A. Antonova "Pharmaceutical Chemistry", Moscow, Medicine 1985, pp. 21-23.
Khramkina M.N. "Workshop on organic synthesis", Publishing house "Chemistry", Leningrad branch, 1977 (Chapter II on pp. 51-55).
A.D. Nechaev, F.R. Ermakhanova, G.A. Nosov, "Purification of substances by fractional crystallization method using binary solvents", Advances in chemistry and chemical technology, 2007.
Lian Yu: "Amorphous pharmaceutical solids: preparation, characterization and stabilization", Advanced Drug Delivery Reviews, 2001, v.48, p. 27-42 (p. 28, 1.Introduction; DOI:10.1016/S0169-409X(01)00098-9.
Office Action issued in corresponding Russian Patent Application No. 2019132946, dated Mar. 12, 2021.
Yoko Kawaguchi et al.: "Drug and crystal polymorphism", Journal of Human Environmental Engineering, vol. 4, No. 2, 2002, pp. 310-317.
Pharmaceutical Affairs Bureau Notification vol. 568, 2001.
Ohshima, "Crystallization of Polymorphs and Pseudo-polymorphs and its Control", Pharm Stage, 2007, vol. 6, No. 10, pp. 48-53.

(Continued)

*Primary Examiner* — Noble E Jarrell
(74) *Attorney, Agent, or Firm* — Locke Lord LLP; Scott D. Wofsy; Zhibin Li

(57) ABSTRACT

The present invention relates to a novel crystalline 3-phenyl-4-propyl-1-(pyridin-2-yl)-1H-pyrazol-5-ol hydrochloride, a method for preparing the compound, and a pharmaceutical composition containing the compound as an active ingredient.

9 Claims, 8 Drawing Sheets

(56) References Cited

OTHER PUBLICATIONS

Takada, "API form screening and selection in drug discovery stage", Pharm Stage, 2007, vol. 6, No. 10, pp. 20-25.
Approach to Crystal Polymorph in Process Research of New Drug, Journal of Synthetic Organic Chemistry, vol. 65(9), JPN7018003451, 2007, pages pp. 907-913.
Byrn, S., Pfeiffer, R., Ganey, M., Hoiberg, C., & Poochikian, G. (1995). Pharmaceutical Research, 12(7), 945-954.

* cited by examiner

CRYSTALLINE SOLID COMPOUND OF 3-PHENYL-4-PROPYL-1-(PYRIDIN-2-YL)-1H-PYRAZOL-5-OL HYDROCHLORIDE

CROSS REFERENCE TO RELATED APPLICATIONS

This application is a U.S. National Phase Application filed under 35 U.S.C. § 371, based on International PCT Patent Application No. PCT/KR2018/004604, filed Apr. 20, 2018, which application claims priority to Korean Patent Application No. KR 10-2017-0050924 filed on Apr. 20, 2017. The entire contents of these applications is incorporated herein by reference in their entirety.

TECHNICAL FIELD

The present invention relates to a novel crystalline solid compound, 3-phenyl-4-propyl-1-(pyridin-2-yl)-1H-pyrazol-5-ol hydrochloride, a method for preparing the compound, and a pharmaceutical composition containing the compound as an active ingredient.

BACKGROUND ART 3-phenyl-4-propyl-1-(pyridin-2-yl)-1H-pyrazol-5-ol hydrochloride, represented by the following Formula 1, (hereinafter abbreviated as "hydrochloride compound") or 3-phenyl-4-propyl-1-(pyridin-2-yl)-1H-pyrazol-5-ol, represented by the following Formula 2, (hereinafter, abbreviated as "free base compound") was first synthesized and reported in Korean Patent No. 10-1280160 (Patent Document 1).

[Formula 1]

[Formula 2]

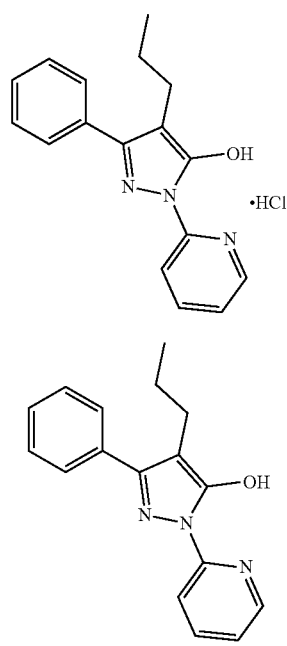

In addition, Korean Patent No. 10-1280160 (Patent Document 1), Korean Patent No. 10-1633957 (Patent Document 2) and Korean Patent Application No. 10-2017-0024083 (Patent Document 3) identified that the compound represented by Formula 1 or 2 has excellent inhibition activity against reactive oxygen species (ROS). In addition, these documents reported, based on the pharmacological mechanism, that the compound represented by Formula 1 or 2 is effective as an active ingredient of pharmaceutical compositions for the treatment of osteoporosis, kidney diseases and ocular diseases.

In addition, Korean Patent No. 10-1633957 (Patent Document 2) discloses a method for producing the compound represented by Formula 1 or Formula 2. Specifically, in accordance with the production method disclosed in Patent Document 2, 2-propyl-3-oxo-3-phenylpropionic acid ethyl ester and 2-hydrazinopyridine are heated and refluxed in an ethanol solvent, and the produced solid is washed with hexane and ethyl acetate, and dried in a vacuum to prepare the free base compound represented by Formula 2. In addition, the prepared free base compound is dissolved in diethyl ether, a HCl/diethyl ether solution is added dropwise thereto at 0° C., and the resulting solid is washed with hexane and ethyl acetate, and dried in a vacuum to prepare the hydrochloride compound represented by Formula 1.

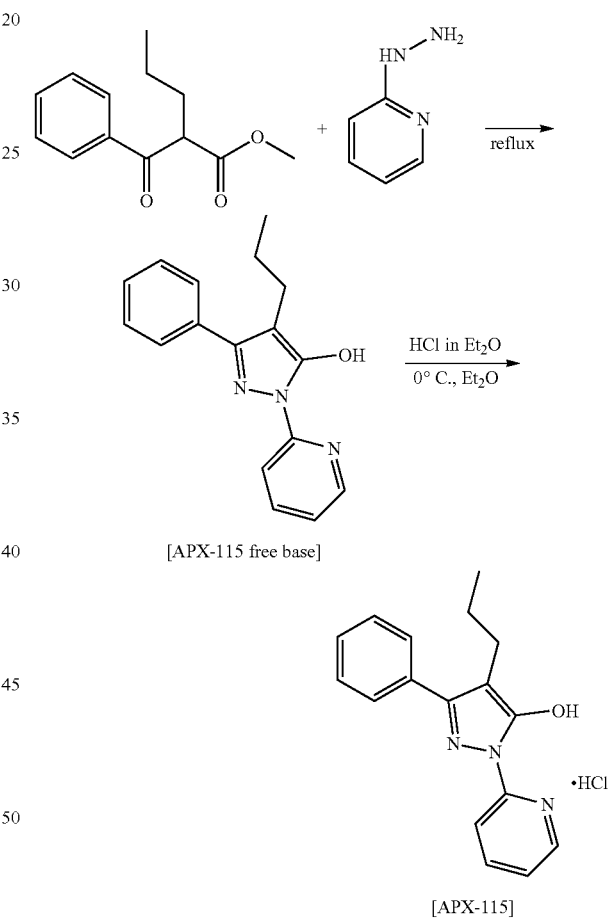

[APX-115 free base]

[APX-115]

In Patent Documents 1 and 2, the compound represented by Formula 1 or 2 is obtained as a non-crystalline solid compound, rather than a crystalline compound.

Meanwhile, amorphous or non-crystalline compounds have a larger particle surface area than crystalline compounds. Thus, the amorphous or non-crystalline compound has the advantage of excellent kinetic solubility in a solvent, but has the disadvantage of low stability compared to crystalline compounds because it does not have lattice energy due to crystallization.

In addition, the crystalline compound has a certain (unique) crystal pattern. The pattern may include a single crystalline form or a polymorphic form including two or more thereof. In addition, the polymorphic compounds may be different in terms of water content (hygroscopicity) and the like, as well as physical properties, such as solubility and melting point. In addition, when a pharmaceutical ingredient is a polymorphic compound, it may affect the release and disintegration of the preparation (formulation) due to the change in the crystal form, which may also affect the absolute oral absorption rate.

That is, polymorphic compounds may have different crystal forms even though they have the same chemical structure and thus may differ with respect to the stability and physiological activity of the compounds. In particular, polymorphic compounds used for pharmaceutical applications may have a great influence on the ease of preparation of pharmaceutical ingredients, solubility, storage stability, ease of preparation of final drugs and in vivo pharmacological activity, depending on the crystal form. Therefore, it is very important to select the crystalline form required for pharmaceutical ingredients according to the route of administration, dosage and the like. The criteria for the selection of general crystalline drugs are determined depending on the physicochemical properties of the crystalline form. For example, the most thermodynamically stable crystalline forms may be selected, crystalline forms optimized for the preparation of pharmaceutical ingredients and drug products may be selected, or crystalline forms capable of improving the solubility and dissolution rate of drugs or changing the pharmacokinetic properties thereof may be selected.

PRIOR ART DOCUMENT

Patent Document (Patent Document 1) Korean Patent No. 10-1280160
(Patent Document 2) Korean Patent No. 10-1633957
(Patent Document 3) Korean Patent Application No. 10-2017-0024083

DISCLOSURE

Technical Problem

The present inventors completed the present invention by preparing a new crystalline compound of the hydrochloride compound represented by Formula 1, which is used as a pharmaceutical ingredient, has excellent physical properties and stability, and can be thermodynamically stabilized in order to prevent crystal (polymorphic) transition due to changes over time under storage conditions.

Therefore, the present invention has been made in view of the above problems, and it is an object of the present invention to provide a novel crystalline hydrochloride compound represented by the following Formula 1:

[Formula 1]

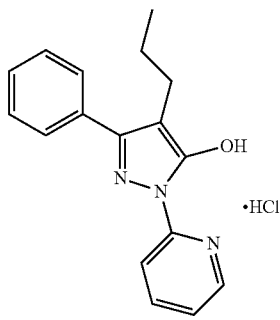

It is another object of the present invention to provide a method for preparing the crystalline hydrochloride compound represented by Formula 1.

It is a further object of the present invention to provide a pharmaceutical composition containing the crystalline hydrochloride compound represented by Formula 1 as an active ingredient.

Technical Solution

In accordance with an aspect of the present invention, the above and other objects can be accomplished by the provision of a crystalline hydrochloride compound represented by the following Formula 1, having a maximum endothermic temperature, measured with a differential scanning calorimeter (DSC), of 134.25±3° C.

[Formula 1]

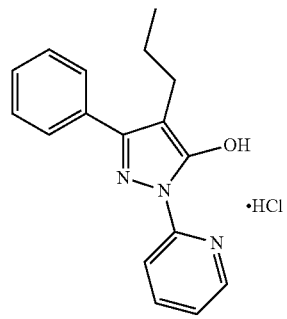

In a preferred embodiment of the present invention, the crystalline hydrochloride compound represented by Formula 1 may have 2θ diffraction angles (2θ±0.2°) having a relative intensity of 15% or higher, obtained through X-ray powder diffraction analysis, of 7.15, 10.72, 13.36, 15.99, 16.39, 16.71, 17.14, 19.61, 21.50, 21.82, 23.46, 24.08, and 25.91.

In accordance with another aspect of the present invention, there is provided a method of preparing the crystalline hydrochloride compound represented by Formula 1 including:

a) reacting 2-propyl-3-oxo-3-phenylpropionic acid ethyl ester with 2-hydrazinopyridine to obtain a crude product;

b) dissolving the crude product in normal hexane and then slowly cooling the resulting solution to −20° C. to −10° C. to produce a solid;

c) filtering, washing and drying the resulting solid to obtain a non-crystalline free base compound;

d) adding the non-crystalline free base compound to a mixed solvent containing acetonitrile and distilled water in the same amount and vigorously stirring the resulting mixture at 20° C. to 25° C. to produce a crystal;

e) filtering, washing and drying the resulting crystal to obtain a crystalline free base compound represented by Formula 2;

f) reacting the crystalline free base compound with a hydrochloric acid-isopropyl ether solution to produce a hydrochloride solid;

g) adding the hydrochloride solid to a mixed solvent containing tert-butyl ether and toluene in the same amount and vigorously stirring the resulting mixture at 5 to 10° C. to produce a crystal; and h) filtering, washing and drying the resulting crystal to obtain a crystalline hydrochloride compound represented by the following Formula 1.

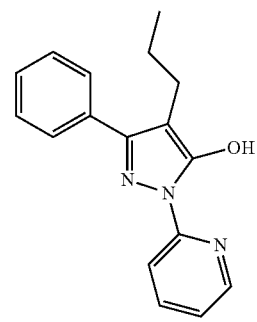

[Formula 2]

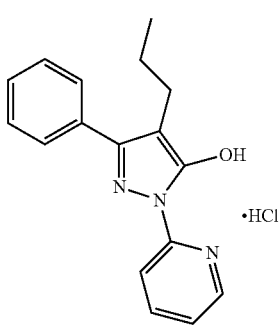

[Formula 1]

In accordance with another aspect of the present invention, there is provided a pharmaceutical composition for the prevention or treatment of a disease mediated by reactive oxygen species (ROS), containing the crystalline hydrochloride compound represented by Formula 1 as an active ingredient.

In accordance with another aspect of the present invention, there is provided a method for treating, preventing or alleviating a disease mediated by reactive oxygen species (ROS), the method including administering an effective amount of the crystalline hydrochloride compound represented by Formula 1 to a subject in need of the same.

In accordance with another aspect of the present invention, there is provided the use of the crystalline hydrochloride compound represented by Formula 1 for the preparation of a drug for treating, preventing or alleviating a disease mediated by reactive oxygen species (ROS).

In accordance with another aspect of the present invention, there is provided the crystalline hydrochloride compound represented by Formula 1 useful for treating, preventing or alleviating a disease mediated by reactive oxygen species (ROS).

In a preferred embodiment of the present invention, the disease mediated by reactive oxygen species (ROS) may be osteoporosis.

In a preferred embodiment of the present invention, the disease mediated by reactive oxygen species (ROS) may be at least one kidney disease selected from the group consisting of diabetic nephropathy, hypertensive nephropathy, glomerulonephritis, pyelonephritis, interstitial nephritis, lupus nephritis, polycystic kidney disease and renal failure.

In a preferred embodiment of the present invention, the disease mediated by reactive oxygen species (ROS) may be at least one ocular disease selected from the group consisting of diabetic retinopathy (DR), diabetic macular edema, age-related macular degeneration, retinopathy of prematurity (ROP), polypoidal choroidal vasculopathy, ischemic proliferative retinopathy, retinitis pigmentosa, cone dystrophy, proliferative vitreoretinopathy (PVR), retinal artery occlusion, retinal vein occlusion, pterygium, retinitis, keratitis, conjunctivitis, uveitis, Leber hereditary optic neuropathy, retinal detachment, retinal pigment epithelial detachment, neovascular glaucoma, corneal neovascularization, retinal neovascularization, choroidal neovascularization (CNV), and viral infection.

In a preferred embodiment of the present invention, the pharmaceutical composition may be formulated into a formulation form selected from the group consisting of a powder, a granule, a tablet, a capsule, a suspension, an emulsion, a syrup, an aerosol, an ointment, a cream, a suppository, an eye drop and an injection.

Advantageous Effects

The crystalline hydrochloride compound represented by Formula 1 provided by the present invention is a novel substance that has not been reported in the literature and has remarkably excellent heat and moisture stability compared to non-crystalline hydrochloride compounds.

In addition, the crystalline hydrochloride compound provided by the present invention has excellent stability when compared to various crystalline acid addition salt compounds prepared by adding an acid other than hydrochloric acid.

In addition, the crystalline hydrochloride compound provided by the present invention not only has physical properties advantageous for drug preparation, but also has excellent stability to heat and moisture, and the drug thus prepared is stably preserved for a period longer than the shelf life without causing decomposition of the active ingredient or polymorphic transition.

Therefore, the crystalline hydrochloride compound provided by the present invention is useful as an active ingredient in the preparation of drugs for the prevention or treatment of osteoporosis, kidney diseases and ocular diseases. Specifically, the crystalline hydrochloride compound can be easily used as a pharmaceutical ingredient of a drug formulated into an oral preparation, an injectable preparation or an eye drop.

BEST MODE

The present invention is directed to a novel crystalline hydrochloride compound, a method for preparing the compound, and a pharmaceutical composition containing the compound as an active ingredient.

The crystalline hydrochloride compound characterized by the present invention is a novel substance that has not been reported in the literature, and has physical properties advantageous for drug preparation, is stable to heat and moisture and secures sufficient stability to prevent decomposition of the active ingredient or polymorphic transition during flow storage.

The crystalline hydrochloride compound provided by the present invention is an acid addition salt compound in which hydrochloric acid is added to the 3-phenyl-4-propyl-1-(pyridin-2-yl)-1H-pyrazol-5-ol, a mother molecule, as shown in the following Formula 1.

[Formula 1]

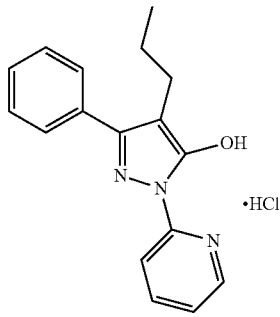

Figure 1:
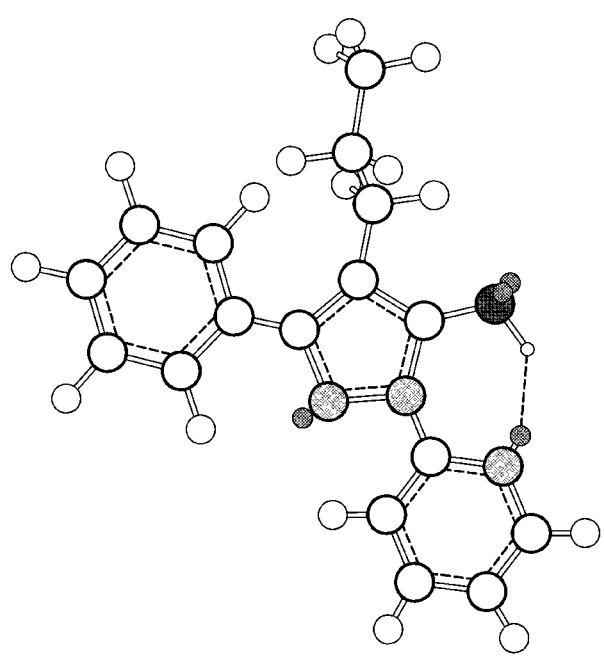
FIG. 1 is an image showing a molecular model of 3-phenyl-4-propyl-1-(pyridin-2-yl)-1H-pyrazol-5-ol.

However, the pyridine group of the mother molecule, which forms the acid addition salt, is a relatively weak base, and the hydroxy group (—OH) at the position C5 of pyrazole can form a hydrogen bond with the nitrogen atom (N) of the pyridine. For this reason, the basicity of pyridine may be weaker than in a general case. This can be seen from the molecular model of FIG. 1. FIG. 1 is an image showing a molecular model of a 3-phenyl-4-propyl-1-(pyridin-2-yl)-1H-pyrazol-5-ol free base which has the most stable form capable of minimizing molecular mechanical energy. It can be seen from the image that the hydroxy group at position C5 of pyrazole forms a hydrogen bond with the nitrogen atom of the pyridine.

The results of experiments conducted by the present inventors showed that hydrogen chloride (HCl) is continuously detached from the non-crystalline hydrochloride compound prepared by a conventional preparation method. As a result, a compound represented by the following Formula 3 is formed as a decomposition product.

[Formula 3]

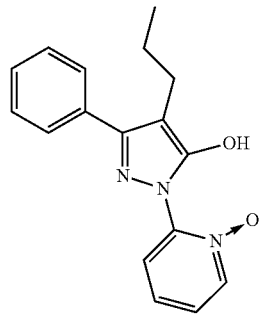

3-phenyl-4-propyl-1-(pyridin-2-yl)-1H-pyrazol-5-ol free base has a high possibility of creating the decomposition product represented by Formula 3 because of the lower melting point thereof compared to pharmaceutically acceptable salt compounds. In addition, as the time of exposure to moisture or heat increases, various impurities including the decomposition product of Formula 3 may be produced.

The requirements of crystalline hydrochloride compounds for drug applications include the following. First, crystalline hydrochloride compounds should be physically stable for application to a process for the synthesis of pharmaceutically acceptable salts or a process for formulation of pharmaceutical ingredients. Second, crystalline hydrochloride compounds should not easily transit to the crystalline form over time during storage and distribution. Third, crystalline hydrochloride compounds should be capable of minimizing the formation of impurities including the N—O compound of pyridine represented by Formula 3 during storage and distribution.

Thus, the present inventors studied to select an acid addition salt compound capable of further dynamically stabilizing a 3-phenyl-4-propyl-1-(pyridin-2-yl)-1H-pyrazol-5-ol free base. That is, the present inventors prepared various crystalline hydrochloride compounds and various crystalline hydrochloride compounds added with pharmaceutically acceptable acids having higher acidity than hydrochloric acid (HCl) and no volatility, and conducted experiments to compare the stability between the prepared acid addition salt compounds. It may be predicted that, compared to crystalline hydrochloride compounds added with hydrochloric acid, acid addition salt compounds, which are added with an acid having a pKa value greater than the pKa values of pyridine and hydrochloric acid, and being non-volatile, can effectively inhibit the release (desorption) of acid from the mother molecule. However, the comparative experiments of the present inventors showed unexpected results in that, among the various crystalline acid addition salt compounds based on 3-phenyl-4-propyl-1-(pyridin-2-yl)-1H-pyrazol-5-ol as the mother molecule, the crystalline hydrochloride compound is the most stable under drug storage conditions [See the following Experimental Example 2].

Therefore, the crystalline hydrochloride compound provided by the present invention, which is a hydrochloride compound added with hydrochloric acid, is the most stable among various crystalline acid addition salt compounds. Thus, the crystalline hydrochloride compound can be used as an active ingredient of a drug so that the active ingredient is not decomposed but is stably maintained even when stored for a long period of time of the shelf life.

The present invention also provides a method for preparing a crystalline hydrochloride compound. Specifically, the method for preparing a crystalline hydrochloride compound according to the present invention includes:

a) reacting 2-propyl-3-oxo-3-phenylpropionic acid ethyl ester with 2-hydrazinopyridine to obtain a crude product;

b) dissolving the crude product in normal hexane and then slowly cooling the resulting solution to −20 to −10° C. to produce a solid;

c) filtering, washing and drying the resulting solid to obtain a non-crystalline free base compound;

d) adding the non-crystalline free base compound to a mixed solvent containing acetonitrile and distilled water in the same amount and vigorously stirring the resulting mixture at 20 to 25° C. to produce a crystal;

e) filtering, washing and drying the resulting crystal to obtain a crystalline free base compound represented by Formula 2;

f) reacting the crystalline free base compound with a hydrochloric acid-isopropyl ether solution to produce a hydrochloride solid;

g) adding the hydrochloride solid to a mixed solvent containing tert-butyl ether and toluene in the same amount and vigorously stirring the resulting mixture at 5 to 10° C. to produce a crystal; and h) filtering, washing and drying the resulting crystal to obtain a crystalline hydrochloride compound represented by the following Formula 1.

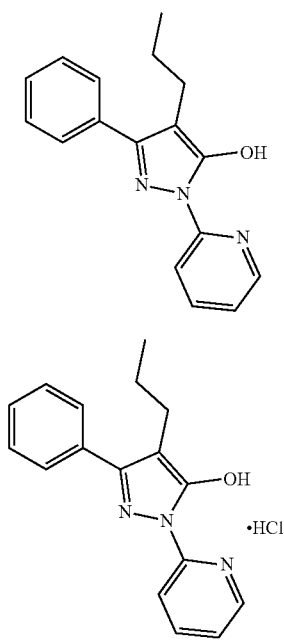

[Formula 2]

[Formula 1]

The preparation method of the crystalline hydrochloride compound according to the present invention will be described in each step in more detail.

In step a), a crude product is prepared according to the manufacturing method disclosed in Korean Patent No. 10-1633957 (Patent Document 2).

The step b) is a process of solidifying the crude product and includes dissolving the crude product in normal hexane and then cooling the solution to produce a solid. In the process of dissolving the crude product, slight heating may be required for complete dissolution and the heating may be appropriately performed within the temperature range of 50° C. to 60° C. The cooling may be suitably performed within the temperature range of −20° C. to −10° C. When the cooling temperature is excessively high, the production rate of the solid may be slow and the yield may be low, and when the cooling temperature is excessively low, crystals may not be produced in the subsequent crystallization process.

In step c), the resulting solid is filtered, washed and dried to obtain a non-crystalline free base compound. The washing may be performed using, as a solvent, normal hexane cooled to 0° C. to 10° C. The drying may be performed at room temperature, or may be carried out by vacuum-drying at 30° C. to 40° C.

The step d) is a process of crystallizing the non-crystalline free base compound. Specifically, the non-crystalline free base compound is added to a mixed solvent containing acetonitrile and distilled water at a weight ratio of 1:1 and vigorously stirred at 20° C. to 25° C. to produce crystals. The weight ratio of the acetonitrile and distilled water may be a weight ratio of 1:0.5 to 1:2.

The step e) is a process of filtering the resulting crystals, washing the crystals with a solvent and drying the same to obtain a crystalline free base compound. The washing solvent used herein is a mixed solvent containing acetonitrile and distilled water at a weight ratio of 1:1, and the solvent is preferably cooled to 0 to 10° C. The drying may be carried out by a conventional drying method, for example, lyophilization, rotary evaporation drying, spray drying, vacuum drying or fluid bed drying, and specifically, may be carried out through vacuum drying. Preferably, the drying may be carried out by vacuum-drying at 30° C. to 40° C.

The step f) is a process of reacting the crystalline free base compound with hydrochloric acid to produce a solid hydrochloric acid addition salt. The hydrochloride production reaction is carried out in an isopropyl ether solvent. The hydrochloric acid may be diluted with isopropyl ether to prepare a solution having a 0.5 to 2M concentration. The reaction temperature is preferably maintained at −10° C. to 10° C., more preferably 0° C. to 5° C.

The step g) is a process of crystallizing the hydrochloride solid. Specifically, the crystalline hydrochloride compound is added to a mixed solvent containing tert-butyl ether and toluene at a weight ratio of 1:1, and vigorously stirred at 5 to 10° C. to produce crystals.

The step h) is a process of filtering, washing and drying the resulting crystals to obtain the crystalline hydrochloride compound. The washing solvent is a mixed solvent containing tert-butyl ether and toluene at a weight ratio of 1:1, and the solvent is preferably cooled to 0° C. to 10° C. The drying may be carried out by a conventional drying method, for example, lyophilization, rotary evaporation drying, spray drying, vacuum drying or fluid bed drying, and specifically, may be carried out by vacuum drying. Preferably, the drying may be carried out by vacuum-drying at 30° C. to 40° C.

Also, the present invention provides a pharmaceutical composition containing the crystalline hydrochloride compound as an active ingredient.

According to Patent Documents 1 to 3, a non-crystalline hydrochloride compound is effective as an active ingredient of a pharmaceutical composition for treating a disease mediated by reactive oxygen species (ROS), particularly, osteoporosis, kidney diseases and ocular diseases. Therefore, the crystalline hydrochloride compound provided by the present invention also has the activity of inhibiting the generation of reactive oxygen species (ROS), and thus, based on this pharmacological mechanism, a pharmaceutical composition containing the crystalline hydrochloride compound as an active ingredient can be used for the treatment or prevention of osteoporosis, a kidney disease and an ocular disease.

The kidney disease may be selected from the group consisting of diabetic nephropathy, hypertensive nephropathy, glomerulonephritis, pyelonephritis, interstitial nephritis, lupus nephritis, polycystic kidney disease and renal failure.

The ocular disease may be selected from the group consisting of diabetic retinopathy (DR), diabetic macular edema, age-related macular degeneration, retinopathy of prematurity (ROP), polypoidal choroidal vasculopathy, ischemic proliferative retinopathy, retinitis pigmentosa, cone dystrophy, proliferative vitreoretinopathy (PVR), retinal artery occlusion, retinal vein occlusion, pterygium, retinitis, keratitis, conjunctivitis, uveitis, Leber hereditary optic neuropathy, retinal detachment, retinal pigment epithelial detachment, neovascular glaucoma, corneal neovascularization, retinal neovascularization, choroidal neovascularization (CNV), and viral infection.

The pharmaceutical composition of the present invention contains a crystalline hydrochloride compound as an active ingredient. The content of the active ingredient may be determined in consideration of the age, body weight or the like of the patient, and may generally fall within the range from 0.01 to 10% by weight based on the total amount of the pharmaceutical composition.

In addition, the pharmaceutical composition of the present invention may include pharmaceutically acceptable additives such as carriers, diluents, binders, disintegrants, lubricants, pH adjusters, antioxidants and dissolution aids within the range that does not impair the effect of the active ingredient. Examples of pharmaceutically acceptable additives that can be used to formulate the pharmaceutical composition of the invention include microcrystalline cellulose, xylitol, erythritol, methyl cellulose, polyvinylpyrrolidone, starch, acacia, alginate, gelatin, lactose, dextrose, sucrose, propylhydroxybenzoate, cellulose, water, methylhydroxybenzoate, magnesium stearate, talc, sorbitol, mannitol, maltitol, calcium phosphate, calcium silicate, mineral oil and the like.

In addition, the pharmaceutical composition of the present invention may be formulated into a formulation form selected from the group consisting of a powder, a granule, a tablet, a capsule, a suspension, an emulsion, a syrup, an aerosol, an ointment, a cream, a suppository, an eye drop and an injection in accordance with conventional preparation methods. There is no particular limitation as to the formulation form in the present invention.

In addition, water for injection may be used for the preparation of an eye drop or injection composition according to the present invention. Eye drops or injections containing pharmaceutically acceptable salts may optionally contain, without limitation, isotonic agents, buffers, osmotic agents and the like, which are commonly used in the art.

MODE FOR INVENTION

Hereinafter, the configurations and effects of the present invention will be described in more detail with reference to examples. However, the following examples are provided only for illustration and should not be construed as limiting the scope of the present invention.

EXAMPLE

Example 1: Preparation of Crystalline Free Base Compound 2-propyl-3-oxo-3-phenylpropionic acid ethyl ester (5.6 g, 51.4 mmol) and 2-hydrazinopyridine (11.5 g, 49 mmol) were injected into a round flask, followed by stirring under a nitrogen atmosphere at 150° C. for 24 hours without a reaction solvent. After the reaction solution was cooled to room temperature, the residue was purified through silica gel column chromatography (30 g; n-Hexane/EtOAc=5/1) and concentrated under reduced pressure. Normal hexane (70 mL) was added to the resulting solid compound, and the solid compound was slowly dissolved by heating and was then slowly cooled to −20° C. for 1 hour. The resulting solid was filtered under reduced pressure and was washed with normal hexane cooled to 0 to 10° C. The washed solid was added to a mixed solvent (100 mL) of acetonitrile and distilled water (1:1) and then stirred vigorously at 25° C. for 1 hour to form crystals. The resulting crystals were filtered, washed with a mixed solvent of acetonitrile and distilled water (1:1), which had been cooled to 10° C. or lower, and vacuum-dried at 40° C. for 12 hours to obtain a crystalline free base compound.

Figure 2:
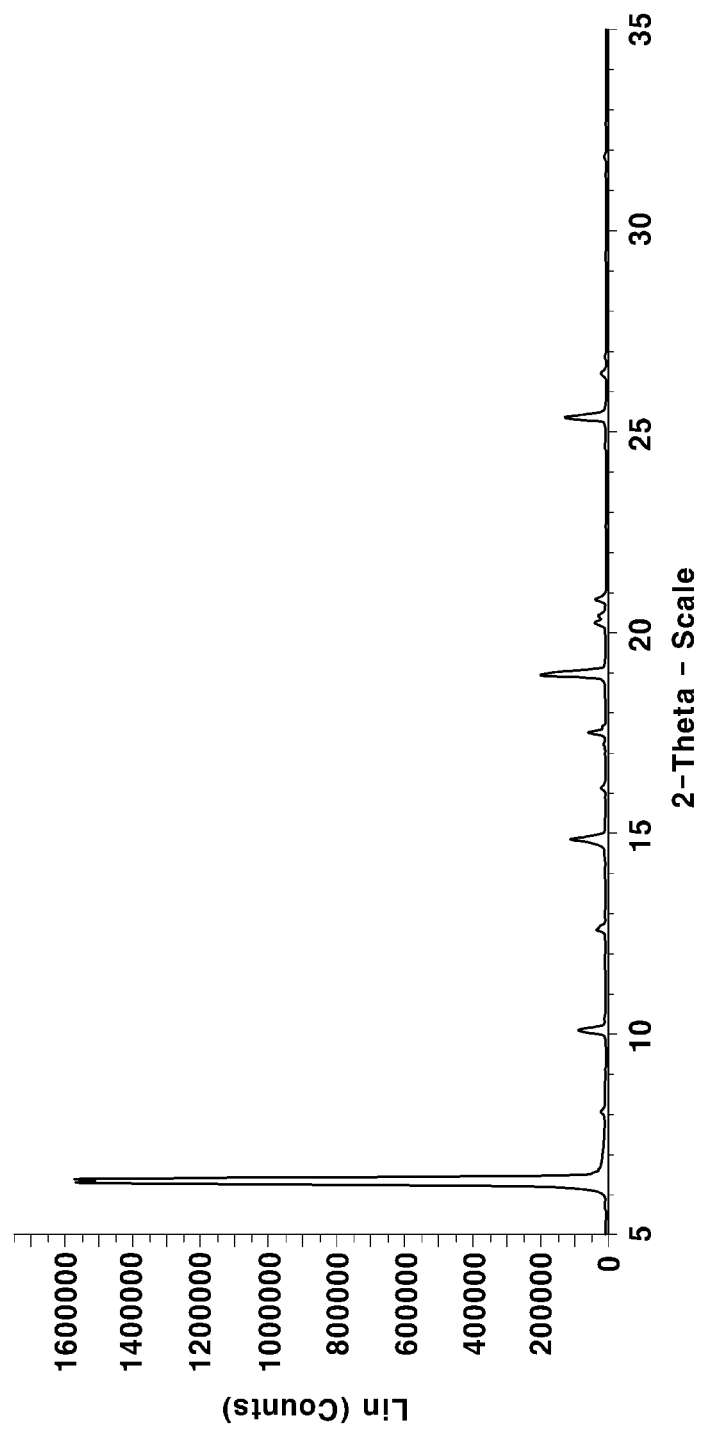
FIG. 2 shows an X-ray powder diffraction pattern of crystalline 3-phenyl-4-propyl-1-(pyridin-2-yl)-1H-pyrazol-5-ol (crystalline free base compound)
Figure 3:
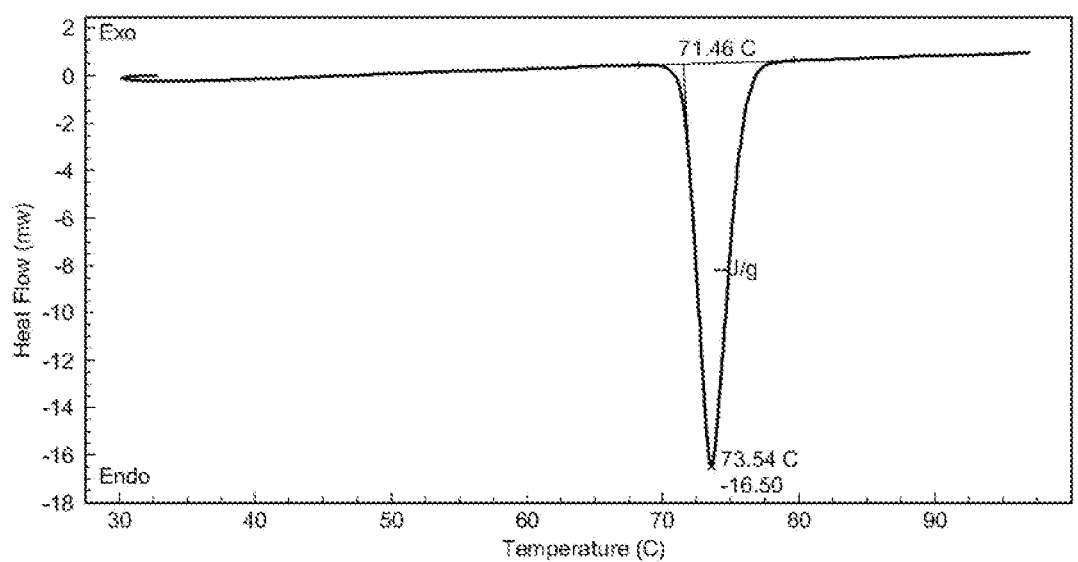
FIG. 3 is a DSC thermal analysis graph of the crystalline free base compound.
Figure 4:
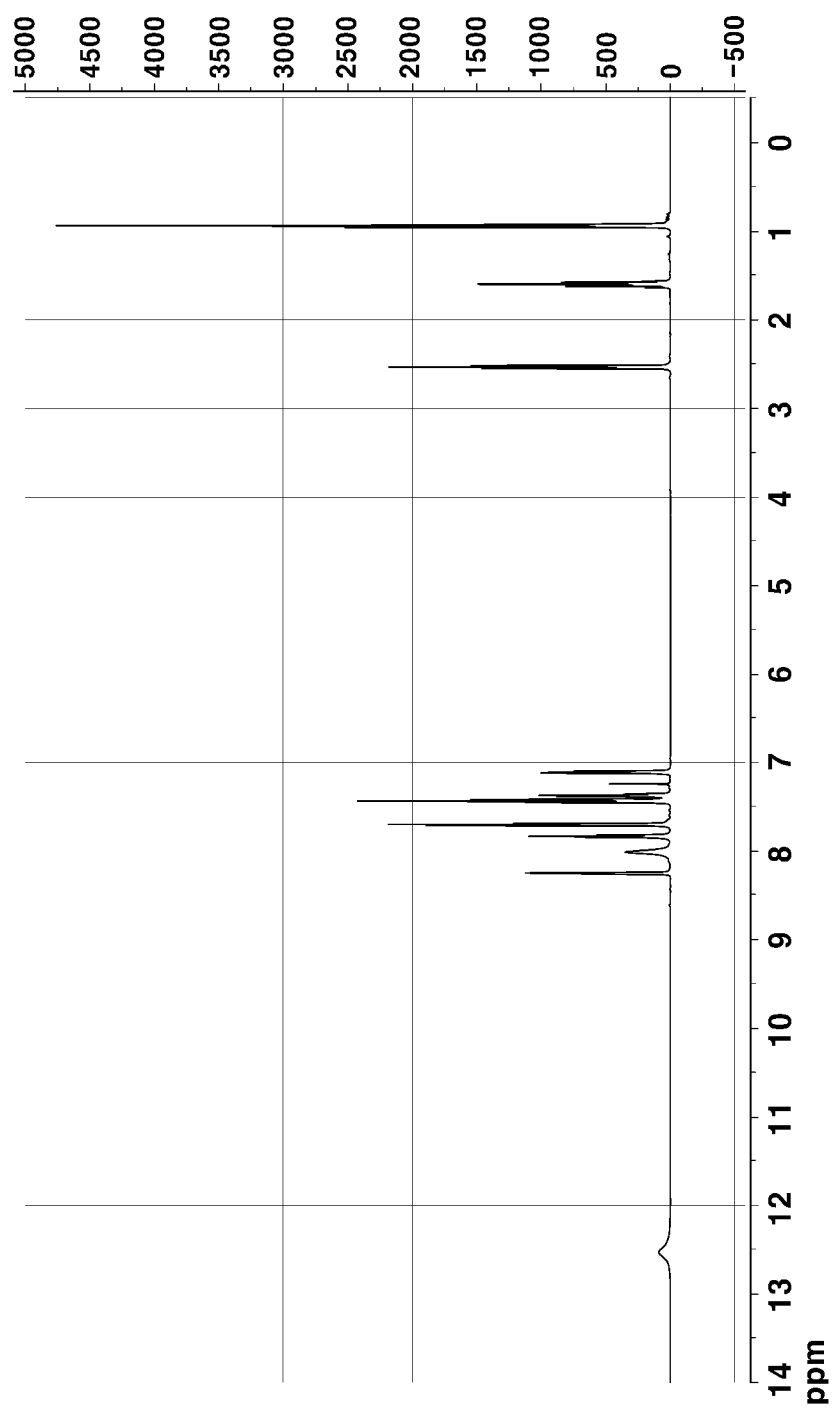
FIG. 4 is a 1H NMR spectrum of the crystalline free base compound.

The X-ray powder diffraction (PXRD) analysis graph, DSC thermal analysis graph and 1H NMR spectra of the crystalline free base compound prepared in Example 1 are shown in FIGS. 2 to 4, respectively.

Example 2. Preparation of Crystalline Hydrochloride Compound

The crystalline free base compound (12.9 g, 46.2 mmol) was injected into a round flask and dissolved in isopropyl ether (300 mL) in a nitrogen atmosphere and a 1 M hydrochloric acid-isopropyl ether solution was then added thereto at 0 to 5° C. for 10 minutes. The reaction solution was stirred at 0 to 5° C. for 1 hour to produce a solid compound. The resulting solid compound was filtered under reduced pressure under a nitrogen atmosphere and washed with isopropyl ether (30 mL), which had been cooled to 10° C. or lower. The washed solid compound was added to tert-butylether and toluene (1:1, 50 mL), followed by stirring vigorously at 5 to 10° C. under a nitrogen atmosphere for 1 hour to form crystals. The resulting crystals were filtered and washed with a mixed solvent of tert-butylether and toluene (1:1), which had been cooled to 10° C. or lower, and dried at 40° C. for 12 hours to obtain a white crystalline hydrochloride compound.

Figure 5:
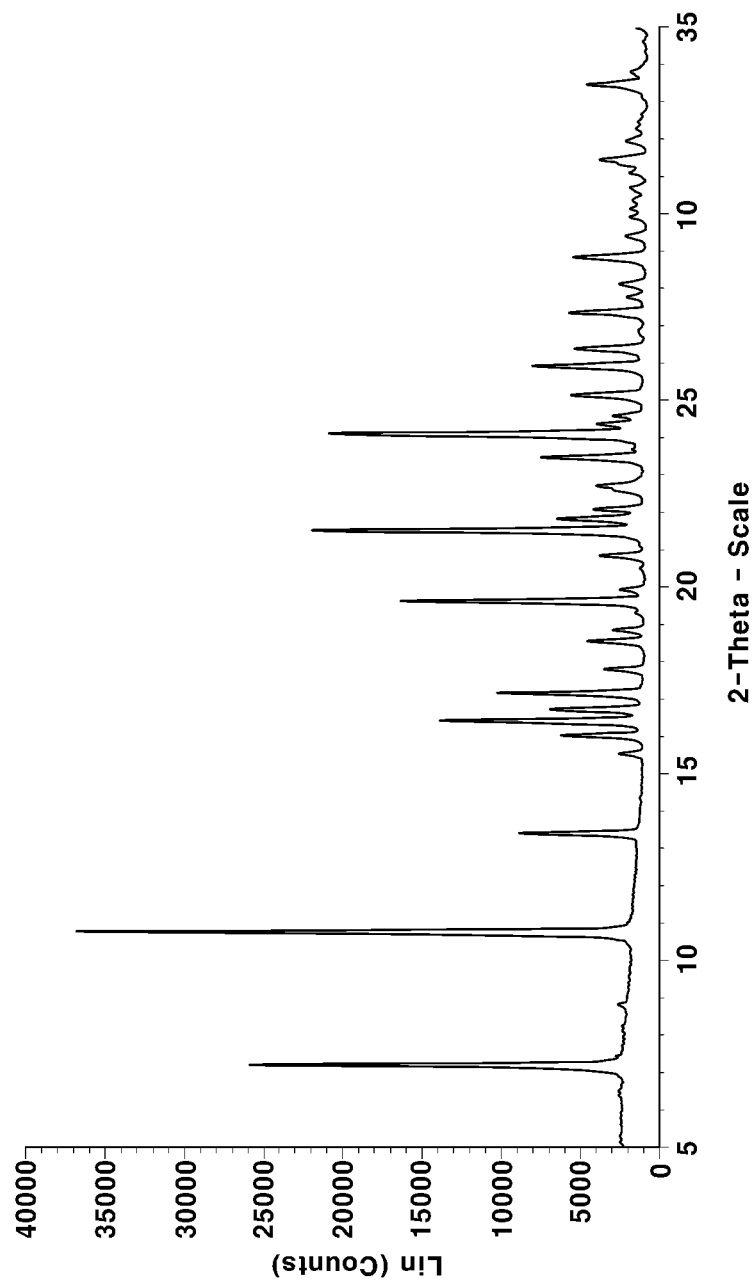
FIG. 5 shows an X-ray powder diffraction pattern of the crystalline 3-phenyl-4-propyl-1-(pyridin-2-yl)-1H-pyrazol-5-ol hydrochloride (crystalline hydrochloride compound)
Figure 6:
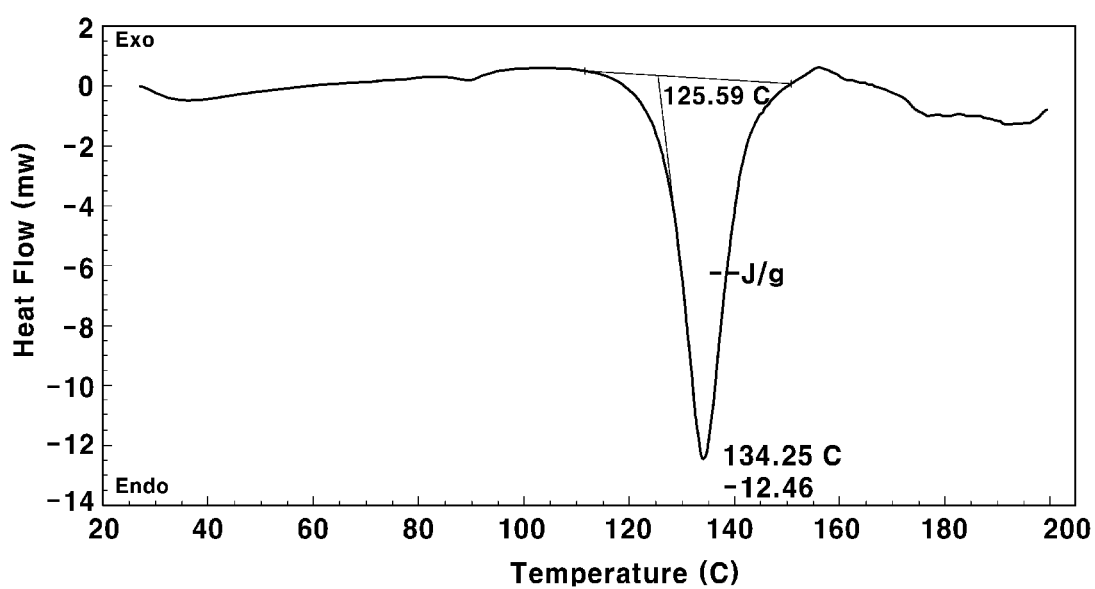
FIG. 6 is a DSC thermal analysis graph of the crystalline hydrochloride compound.
Figure 7:
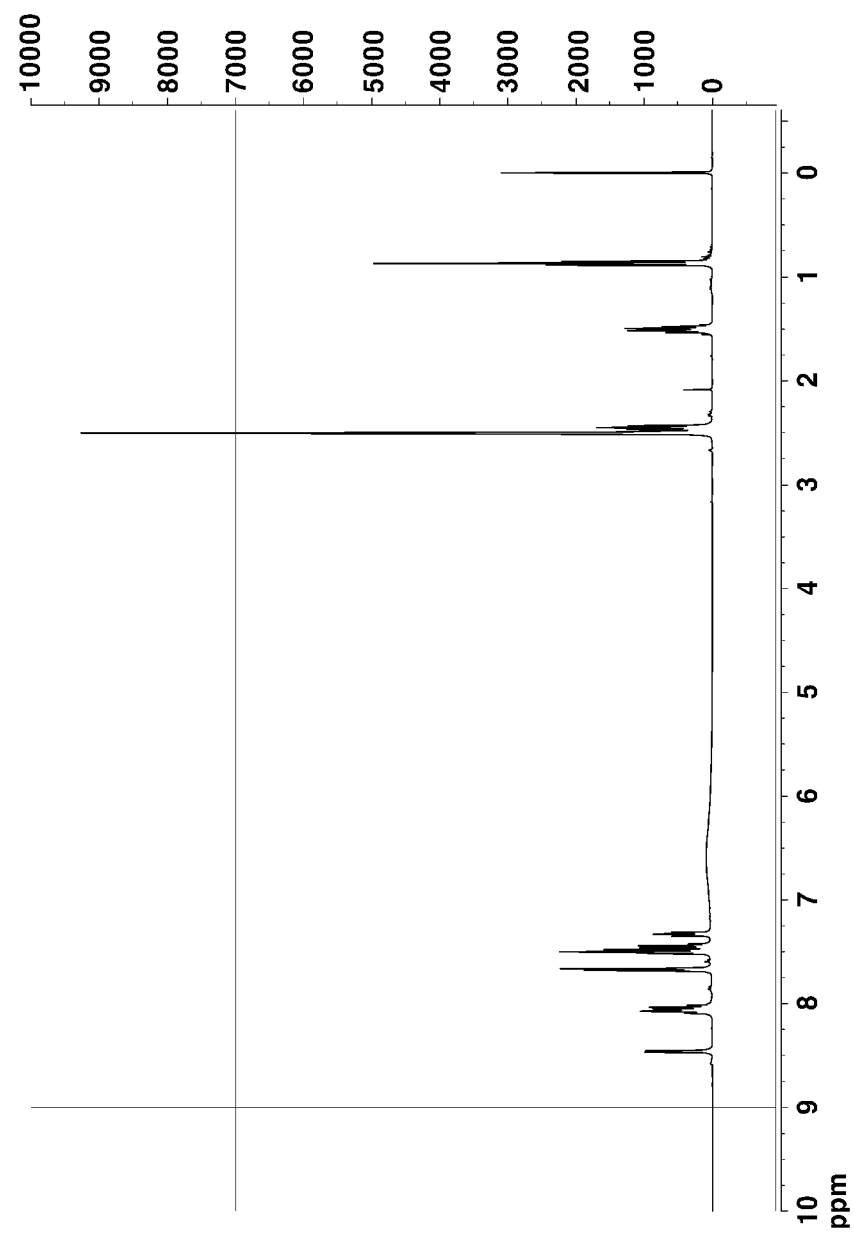
FIG. 7 is a 1H NMR spectrum of the crystalline hydrochloride compound.

X-ray powder diffraction (PXRD) analysis graph, DSC thermal analysis graph and 1H NMR spectra of the crystalline free base compound prepared in Example 2 are shown in FIGS. 5 to 7, respectively.

Comparative Example 1: Preparation of Non-Crystalline Free Base Compound 2-propyl-3-oxo-3-phenylpropionic acid ethyl ester (5.6 g, 51.4 mmol) and 2-hydrazinopyridine (11.5 g, 49 mmol) were injected into a round flask, followed by stirring under a nitrogen atmosphere at 150° C. for 3 days without a reaction solvent. After the reaction solution was cooled to room temperature, the residue was concentrated under reduced pressure, washed with hexane and ethyl acetate, and vacuum-dried to obtain a non-crystalline free base compound.

Comparative Example 2. Preparation of Non-Crystalline Hydrochloride Compound

The non-crystalline free base compound (12.9 g, 46.2 mmol) prepared in Comparative Example 1 was injected into a round flask and dissolved in diethyl ether (300 mL), and a 2M hydrochloric acid-diethyl ether solution was then added thereto at 0 to 5° C. for 10 minutes. The resulting solid compound was filtered under reduced pressure, washed with hexane and ethyl acetate, and vacuum-dried to obtain a non-crystalline hydrochloride compound.

Comparative Example 3. Preparation of Various Crystalline Acid Addition Compounds Acid addition salts were prepared by adding various acids to crystalline 3-phenyl-4-propyl-1-(pyridin-2-yl)-1H-pyrazol-5-ol (crystalline free base). Crystallization methods include various methods known in the literature, for example, reaction crystallization, cooling crystallization, drawing-out crystallization and evaporation crystallization. Crystalline acid addition salt compounds were prepared using about 20 types of acids. Among them, the crystalline acid addition salt compounds prepared through evaporation crystallization are shown in the following Table 1.

Specifically, the crystalline free base compound (12.9 g, 46.2 mmol) was injected into a round flask and the acid shown in Table 1 was added thereto. 20 mL of anhydrous methanol was added to each reaction product and the reaction product was completely dissolved by heating to about 50 to 60° C. The flask was opened, the air inlet thereof was covered with Kimwipes™ tissue paper to enable air passage and wrapped in a rubber band, and the flask was stored in a fume hood for 36 hours. At this time, the temperature inside the fume hood was maintained between 23 and 26° C. The resulting solid was filtered, washed with normal hexane (5 mL), which had been cooled to 10° C. or lower, and then dried in a vacuum to yield a crystalline acid addition salt.

TABLE 1

| Item | Type of acid | Molar ratio of free base:acid |
|---|---|---|
| Sample 1 | Fumaric acid | 1:1 |
| Sample 2 | 1,5-naphthalene disulfonic acid | 1:0.5 (Hemi-salt) |
| Sample 3 | Succinic acid | 1:1 |
| Sample 4 | L-tartaric acid | 1:1 |
| Sample 5 | L-malic acid | 1:1 |

Figure 8:
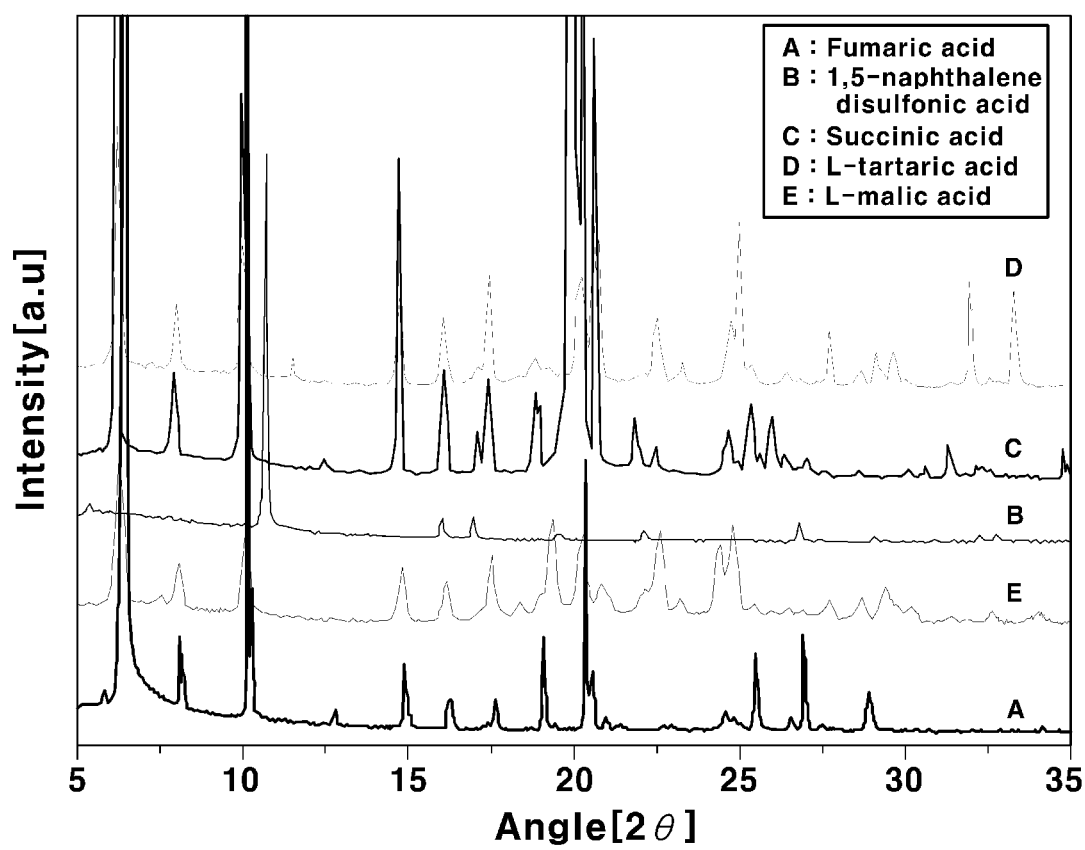
FIG. 8 shows X-ray powder diffraction patterns of various crystalline acid addition salt compounds.

The results of X-ray powder diffraction analysis performed on the crystalline hydrochloride compound prepared in Example 2 and various crystalline acid addition salt compounds prepared in Comparative Example 3 are shown in FIG. 8.

Experimental Example

Experimental Example 1. Hygroscopicity Test

Hygroscopicity comparison experiments were conducted on each of the crystalline free base compound (Example 1), the crystalline hydrochloride compound (Example 2), the non-crystalline free base compound (Comparative Example 1), the non-crystalline hydrochloride compound (Comparative Example 2) and various crystalline acid addition compounds (Comparative Example 3).

The test compounds were exposed in a Petri dish under accelerated storage conditions at a temperature of 40° C. and a relative humidity of 75% for 7 days without sealing. The water content of each test compound was measured using a Karl-Fischer moisture meter. Table 2 summarizes the water content (%) of each test compound measured during the storage period.

TABLE 2

| | | Water content (%) | | | |
|---|---|---|---|---|---|
| Classification | | Initial | 1 day | 3 days | 7 days |
| Free base compound | Crystalline (Example 1) | 0.26 | 0.29 | 0.32 | 0.34 |
| | Non-crystalline (Comparative Example 1) | 0.33 | 1.30 | 2.27 | 2.95 |
| Hydrochloride compound | Crystalline (Example 2) | 0.25 | 0.31 | 0.37 | 0.39 |
| | Non-crystalline (Comparative Example 2) | 0.31 | 1.98 | 3.54 | 7.52 |

TABLE 2-continued

| | | Water content (%) | | | |
|---|---|---|---|---|---|
| Classification | | Initial | 1 day | 3 days | 7 days |
| Crystalline acid addition salt (Comparative Example 3) | Fumarate | 0.28 | 0.34 | 0.38 | 0.40 |
| | Hemi-1,5-naphthalene disulfonate | 0.12 | 0.12 | 0.13 | 0.15 |
| | Succinate | 0.37 | 0.42 | 0.44 | 0.48 |
| | L-tartrate | 0.33 | 0.34 | 0.34 | 0.38 |
| | L-malate | 0.45 | 1.58 | 1.75 | 2.80 |

The results of Table 2 show that, in the case of the free base compound and the hydrochloride compound, the crystalline compound has a lower initial water content and also has a significant difference in water content after 7 days under accelerated storage conditions compared to the non-crystalline compound. Therefore, the crystalline free base compound or the crystalline hydrochloride compound is considerably less hygroscopic and becomes saturated rather than having increased water content over time, and thus is useful as a pharmaceutical ingredient for pharmaceutical application. In addition, it can be seen that, when compared to crystalline acid addition salt compounds added with acids other than hydrochloric acid (Comparative Example 3), crystalline hydrochloride compounds have excellent hygroscopicity compared to crystalline acid addition salts other than crystalline 1,5-naphthalenedisulfonate and crystalline malate.

Experimental Example 2. Stability Comparison Test

Stability comparison experiments were conducted on each of the crystalline free base compound (Example 1), the crystalline hydrochloride compound (Example 2), the non-crystalline free base compound (Comparative Example 1), the non-crystalline hydrochloride compound (Comparative Example 2) and various crystalline acid addition compounds (Comparative Example 3).

The test compound was stored in a chamber for stability measurement under long-term storage conditions at a temperature of 25° C. and a relative humidity of 60% for 6 months. For storage, each test compound was placed in a double polyethylene bag, and the polyethylene bag was filled with a silica gel pouch and was then placed in a small paper box (fiber drum).

The following Table 3 summarizes the results of the measurement of the concentration of the degradation product of Formula 3 and the total impurity concentration by HPLC analysis after storage under long-term storage conditions for 6 months.

[Analytical Conditions of Liquid Chromatography (HPLC)]

Column: 4.6 mm×250 mm, 5 um, 100 Å pore size

Column temperature: 35° C.

Detector: UV Detector (246 nm)

Flow rate: 1.0 mL/min
Time: 55 minutes
Gradient condition of mobile phase:

| Time | Gradient condition of mobile phase (Vol %) | | |
|---|---|---|---|
| | Mobile phase A | Mobile phase B | Mobile phase C |
| 0 min | 50 | 35 | 15 |
| 1 min | 50 | 35 | 15 |
| 37 minutes | 13 | 72 | 15 |
| 38 minutes | 10 | 75 | 15 |
| 43 minutes | 10 | 75 | 15 |
| 44 minutes | 50 | 35 | 15 |
| 55 minutes | 50 | 35 | 15 |

Mobile phase A: Adjusted to pH 2.2 using 25 mM $NaH_2PO_4$ (phosphoric acid)
Mobile phase B: Methanol
Mobile phase C: Acetonitrile

TABLE 3

| Type of salt of Formula 1 | | Concentration of decomposition product of Formula 3 (%) | | Total impurity concentration (%) | |
|---|---|---|---|---|---|
| | | Initial | 6 months | Initial | 6 months |
| Free base compound | Crystalline (Example 1) | 0.05 | 0.09 | 0.32 | 0.47 |
| | Non-crystalline (Comparative Example 1) | 0.06 | 0.65 | 0.26 | 7.58 |
| Hydrochloride compound | Crystalline (Example 2) | 0.03 | 0.08 | 0.28 | 0.45 |
| | Non-crystalline (Comparative Example 2) | 0.05 | 0.92 | 0.35 | 5.87 |
| Crystalline acid addition salt (Comparative Example 3) | Fumarate | 0.07 | 0.27 | 0.45 | 1.35 |
| | Hemi-1,5-naphthalene disulfonate | 0.08 | 0.35 | 0.52 | 1.24 |
| | Succinate | 0.09 | 0.38 | 0.48 | 1.65 |
| | L-tartrate | 0.10 | 0.54 | 0.40 | 1.85 |
| | L-malate | 0.12 | 0.78 | 0.58 | 3.27 |

The results of Table 3 show that, in the case of the free base compound, compared to the crystalline free base compound (Example 1), the non-crystalline free base compound (Comparative Example 1) has a significantly higher concentration of the decomposition product represented by Formula 3. It can be seen that, in the case of the total impurity concentration measured after 6 months, compared to the initial state, the content of non-crystalline free base compound (Comparative Example 1) is significantly increased compared to that of the crystalline free base compound (Example 1). In addition, in the case of the hydrochloride compound, the non-crystalline hydrochloride compound (Comparative Example 2) undergoes detachment of hydrochloric acid (HCl). As a result, it can be seen that the non-crystalline hydrochloride compound (Comparative Example 2) has a significantly higher concentration of the decomposition product represented by Formula 3 compared to the crystalline hydrochloride compound (Example 2). In addition, it can be seen that the non-crystalline hydrochloride compound (Comparative Example 2) has a higher impurity concentration than that of the crystalline hydrochloride compound (Example 2) because the non-crystalline hydrochloride compound (Comparative Example 2) has lower thermodynamic stability even when the concentration of the impurity is compared.

In addition, when compared to a crystalline acid addition salt compound to which an acid other than hydrochloric acid is added, the crystalline hydrochloride compound (Example 2) has a considerably low concentration of the decomposition product represented by Formula 3 and a considerably low impurity concentration compared to the crystalline acid addition salt compound (Comparative Example 3). Therefore, the crystalline hydrochloride compound is the most stable among the various crystalline acid addition salt compounds.

Experimental Example 3. Evaluation of Polymorphic Transition

In order to determine whether or not the polymorphic transition phenomenon occurs under the storage conditions in the crystalline free base compound (Example 1) and the crystalline hydrochloride compound (Example 2), the results of PXRD analysis in the initial state and the possibility of polymorphic transition over time were examined.

Specifically, the test compound was stored in a polyethylene bag in a chamber for stability measurement at a temperature of 40° C. and a relative humidity of 75% for 4 weeks. Also, PXRD and DSC analysis results, measured at the initial state and after 4 weeks, were compared. The comparison results are summarized in Table 4 below.

TABLE 4

| Item | Crystalline free base | | Crystalline hydrochloride salt | |
|---|---|---|---|---|
| | Initial | 4 weeks | Initial | 4 weeks |
| DSC endothermic temperature | 73.54° C. | 72.8° C. | 134.25° C. | 133.4° C. |
| PXRD analysis result | Same crystalline type | | Same crystalline type | |
| Comparison and determination results | No polymorphic transition | | No polymorphic transition | |

The crystalline free base compound (Example 1) and the crystalline hydrochloride compound (Example 2) were subjected to PXRD and DSC 4 weeks after storage. The results showed that no polymorphic transition occurred over time. This indicates that the crystalline free base compound (Example 1) and the crystalline hydrochloride compound (Example 2) are stable compounds.

Experimental Example 4. Physical Property Analysis (1) Powder X-Ray Diffraction (PXRD) Analysis X-ray powder diffraction analysis of the crystalline free base compound and the crystalline hydrochloride compound prepared in Examples 1 and 2 was conducted using Cu-Kα rays on a D8 Advance X-ray powder diffractometer produced by Bruker Corporation. The diffractometer was equipped Dynamic Beam Optimization (DBO) and the amount of current was set to 45 kV and 40 mA. The divergence and scattering slits were set to 1° and the light-receiving slit was set to 0.2 mm. 2θ was measured at 6°/minute from 5 to 35°. Results of PXRD analysis are shown in FIGS. 2 and 5.

In addition, the following Table 5 shows the results of X-ray powder diffraction analysis, more particularly, the 2θ diffraction angle (2θ±0.2°) having a relative intensity of 5% or more in the case of the crystalline free base compound and the 2θ diffraction angle (2θ±0.2°) having a relative intensity of 15% or more in the case of the crystalline hydrochloride compound.

TABLE 5

| Crystalline free base | | | Crystalline hydrochloride salt | | |
|---|---|---|---|---|---|
| Diffraction angle (2θ, °) | d-lattice spacing (Å) | Relative intensity (%) | Diffraction angle (2θ, °) | d-lattice spacing (Å) | Relative intensity (%) |
| 6.30 | 14.0278 | 100.0 | 7.15 | 12.3515 | 70.3 |
| 10.06 | 8.7902 | 5.5 | 10.72 | 8.2494 | 100.0 |
| 14.81 | 5.9750 | 7.0 | 13.36 | 6.6219 | 24.0 |
| 18.95 | 4.6795 | 12.6 | 15.99 | 5.5390 | 16.7 |
| 25.37 | 3.5080 | 8.0 | 16.39 | 5.4052 | 37.4 |
| | | | 16.71 | 5.3023 | 18.7 |
| | | | 17.14 | 5.1686 | 27.9 |
| | | | 19.61 | 4.5226 | 44.4 |
| | | | 21.50 | 4.1297 | 59.6 |
| | | | 21.82 | 4.0708 | 17.4 |
| | | | 23.46 | 3.7893 | 20.3 |
| | | | 24.08 | 3.6927 | 56.5 |
| | | | 25.14 | 3.5396 | 15.0 |
| | | | 25.91 | 3.4356 | 21.6 |
| | | | 27.36 | 3.2574 | 15.4 |

(2) Temperature Differential Scanning Calorimetry (DSC) Analysis

The melting points of the crystalline free base compound and the crystalline hydrochloride compound prepared in Examples 1 and 2 were measured by temperature differential scanning calorimetry (DSC) analysis.

DSC measurements were conducted using DSC N-650 obtained from SCINCO under a nitrogen stream in a sealed pan at a scan rate of 10° C./min from 20° C. to 150° C. The results are shown in FIGS. 3 and 6, respectively.

As can be seen from FIGS. 3 and 6, the crystalline free base compound showed a characteristic endothermic peak at 73.54±3° C. and the crystalline hydrochloride compound showed a characteristic endothermic peak at 134.25±3° C.

In addition, it can be seen that the non-crystalline free base compound prepared in Comparative Example 1 has a non-constant melting point and is completely melted at 60° C. or higher. The non-crystalline hydrochloride compound prepared in Comparative Example 2 also has a non-constant melting point, is slowly melted within a wide temperature range and is completely melted at 160° C. or higher. In consideration of these aspects, it can be seen that the crystalline compound provided by the present invention is a distinguished compound having completely different physicochemical properties from those of the non-crystalline compound.

The experimental results described above show that the crystalline free base compound represented by Formula 2 and the crystalline hydrochloride compound represented by Formula 1 have no hygroscopicity, excellent stability, and a low possibility of polymorphic transition over time and are thus optimized as pharmaceutical ingredients compared to other crystalline acid addition salts and conventional substances.

Certain configurations of the present invention have been disclosed, and those skilled in the art will appreciate that the illustrative detailed description is provided only to describe preferred embodiments, and should not be construed as limiting the scope of the present invention.

Therefore, the actual scope of the present invention is defined by the accompanying claims and equivalents thereto.

The invention claimed is:

1. A crystalline 3-phenyl-4-propyl-1-(pyridin-2-yl)-1H-pyrazol-5-ol hydrochloride represented by the following Formula 1, having a maximum endothermic temperature, measured with a differential scanning calorimeter (DSC), of 134.25±3° C.

[Formula 1]

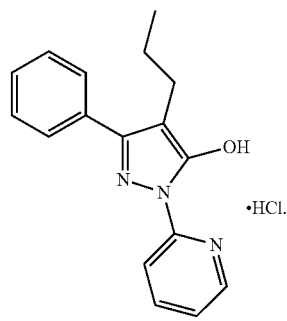

2. The crystalline 3-phenyl-4-propyl-1-(pyridin-2-yl)-1H-pyrazol-5-ol hydrochloride according to claim 1, wherein the crystalline 3-phenyl-4-propyl-1-(pyridin-2-yl)-1H-pyrazol-5-ol hydrochloride has 2θ diffraction angles (2θ±0.2°) having a relative intensity of 15% or higher, obtained through X-ray powder diffraction analysis, of 7.15, 10.72, 13.36, 15.99, 16.39, 16.71, 17.14, 19.61, 21.50, 21.82, 23.46, 24.08, 25.91 and 27.36.

3. A method of preparing a crystalline 3-phenyl-4-propyl-1-(pyridin-2-yl)-1H-pyrazol-5-ol hydrochloride comprising:

a) reacting 2-propyl-3-oxo-3-phenylpropionic acid ethyl ester with 2-hydrazinopyridine to obtain a crude product;

b) dissolving the crude product in normal hexane and then slowly cooling the resulting solution to −20 to −10° C. to produce a solid;

c) filtering, washing and drying the resulting solid to obtain a non-crystalline free base compound;

d) adding the non-crystalline free base compound to a mixed solvent containing acetonitrile and distilled water in the same amount and vigorously stirring the resulting mixture at 20 to 25° C. to produce a crystal;

e) filtering, washing and drying the resulting crystal to obtain a crystalline free base compound represented by Formula 2;

f) reacting the crystalline free base compound with a hydrochloric acid-isopropyl ether solution to produce a hydrochloride solid;

g) adding the hydrochloride solid to a mixed solvent containing tert-butyl ether and toluene in the same amount and vigorously stirring the resulting mixture at 5 to 10° C. to produce a crystal; and h) filtering, washing and drying the resulting crystal to obtain a crystalline hydrochloride compound represented by the following Formula 1

[Formula 2]

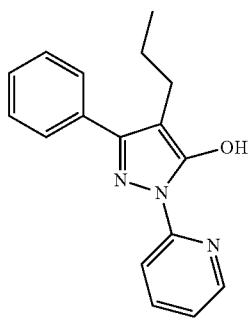

[Formula 1]

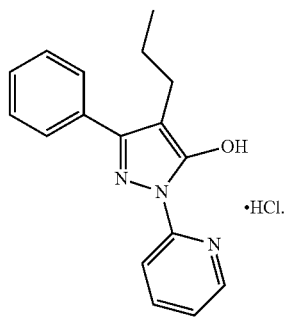

4. A method for treatment of a disease mediated by reactive oxygen species (ROS), the method comprises administering an effective amount of the crystalline 3-phenyl-4-propyl-1-(pyridin-2-yl)-1H-pyrazol-5-ol hydrochloride according to claim 1 to a subject in need thereof, wherein the disease mediated by reactive oxygen species (ROS) is selected from osteoporosis, diabetic nephropathy, diabetic retinopathy (DR) and age-related macular degeneration.

5. A method for treatment of a disease mediated by reactive oxygen species (ROS), the method comprises administering an effective amount of the crystalline 3-phenyl-4-propyl-1-(pyridin-2-yl)-1H-pyrazol-5-ol hydrochloride according to claim 2 to a subject in need thereof, wherein the disease mediated by reactive oxygen species (ROS) is selected from osteoporosis, diabetic nephropathy, diabetic retinopathy (DR) and age-related macular degeneration.

6. A pharmaceutical composition comprising the crystalline 3-phenyl-4-propyl-1-(pyridin-2-yl)-1H-pyrazol-5-ol hydrochloride according to claim 1 and one or more pharmaceutical acceptable additives.

7. The pharmaceutical composition according to claim 6, wherein the pharmaceutical acceptable additives contains one or more of microcrystalline cellulose, xylitol, erythritol, methyl cellulose, polyvinylpyrrolidone, starch, acacia, alginate, gelatin, lactose, dextrose, sucrose, propylhydroxybenzoate, cellulose, water, methylhydroxybenzoate, magnesium stearate, talc, sorbitol, mannitol, maltitol, calcium phosphate, calcium silicate, mineral oil, or a mixture thereof.

8. The pharmaceutical composition according to claim 6, wherein the pharmaceutical composition is formulated into a formulation form selected from the group consisting of a powder, a granule, a tablet, a capsule, a suspension, an emulsion, a syrup, an aerosol, an ointment, a cream, a suppository, an eye drop, or an injection.

9. A crystalline 3-phenyl-4-propyl-1-(pyridin-2-yl)-1H-pyrazol-5-ol hydrochloride comprising 2θ diffraction angles (2θ±0.2°), obtained through X-ray powder diffraction analysis, of 7.15, 10.72, 13.36, 15.99, 16.39, 16.71, 17.14, 19.61, 21.50, 21.82, 23.46, 24.08, 25.91 and 27.36.

* * * * *